United States Patent [19]

Herrinton

[11] Patent Number: 5,220,034
[45] Date of Patent: Jun. 15, 1993

[54] PROTECTED DERIVATIVES OF THE ENONE OF SPECTINOMYCIN

[75] Inventor: Paul M. Herrinton, Kalamazoo, Mich.

[73] Assignee: The Upjohn Company, Kalamazoo, Mich.

[21] Appl. No.: 847,496

[22] Filed: Mar. 13, 1992

Related U.S. Application Data

[63] Continuation of Ser. No. 406,912, Sep. 13, 1989, abandoned.

[51] Int. Cl.$^5$ .................. C07D 497/04; C07D 493/04
[52] U.S. Cl. .......................................... 549/4; 549/16; 549/214; 549/361
[58] Field of Search ........................ 549/4, 16, 214, 361

[56] References Cited

U.S. PATENT DOCUMENTS

| | | | |
|---|---|---|---|
| 4,351,771 | 9/1982 | White et al. | 549/16 |
| 4,420,623 | 12/1983 | White | 549/16 |
| 4,420,624 | 12/1983 | White et al. | 549/16 |
| 4,467,103 | 8/1984 | White et al. | 549/361 |
| 4,730,059 | 3/1988 | White et al. | 549/361 |

OTHER PUBLICATIONS

Greene, *Protective Groups in Organic Synthesis*, John Wiley & Sons, 1981, pp. 21, 39-43, 53, 232, 239, 284 and 285.
Michael M. Rathke et al, "The Preparation and Reactions . . . -Unsaturated Esters", Tet. Let., 41, pp. 4249, 4257 (1972).
S. A. G. de Graaf et al, "Direct Alkylation . . . -Unsaturated Aldehydes", Tet. Let., 17 pp. 1653, 1655 (1974).
J. A. Katzenellenbogen et al, "Regioselectivity in the Alkylation . . . of Copper Dienolates", J. Am. Chem. Soc., 96:17, pp. 5662-5663 (1974).
J. A. Katzenellenbogen et al, "Selectivity . . . Synthesis of Isoprenoid Olefins", J. Am. Chem. Soc., 98:16, pp. 4925-4934 (1976).
P. M. Savu et al, "Selective . . . Regio- and Stereoselectivity", J. Org. Chem., 46, pp. 239-249 (1981).
M. Majewski et al, "Metalated Unsaturated Amides. Regio- . . . -Alkylation", J. Org. Chem., 46, pp. 2029-2045 (1981).
Masafumi Yoshimoto et al, "A New General Method for Carbon-Carbon . . . -Position", Tet. Let., 1, pp. 39-42 (1973).
T. A. Bryson et al, "Enamine Chemistry I. Carbanion Alkylations", Tet. Let., 45, pp. 3963-3966 (1974).
R. B. Gammill et al, "Alkylations of Vinylogous Amides, . . . Potassium Hydride", Synthesis, pp. 401-403 (1978).

Amos B. Smith, III et al, "γ-Alkylation of Lithium . . . αβ-Unsaturated Carbonyl Compounds", Tet. Let. 44, pp. 4193-4196 (1975).
Gilbert R. Stork et al, "The Regiospecific Alkylation of Cyclic . . . of 4-Alkylcyclohexenones", J. Org. Chem., 38, pp. 1775-1776. (1973).

*Primary Examiner*—Joseph Paul Brust
*Assistant Examiner*—Jacqueline Haley
*Attorney, Agent, or Firm*—Sidney B. Williams, Jr.

[57] ABSTRACT

Process for alkylating protected spectinomycin enone derivatives in the gamma position in order to produce intermediates useful in the synthesis of 6'alkylspectinomycins. The intermediate have the formula

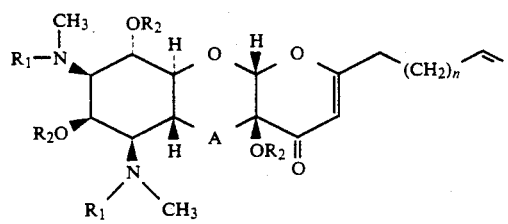

which comprises reacting a compound having the formula

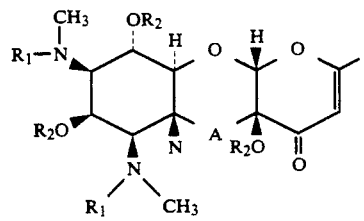

with a strong base and an alkenyl halide, wherein $R_1$ is selected from the group consisting of alkoxycarbonyl, halogenated alkoxycarbonyl, aralkoxycarbonyl, and arylsulfone; $R_2$ is selected from the group consisting of hydrogen, trimethylsilyl (TMS), tetrahydropyran (THP), and triethylsilyl (TES); A is selected from the group consisting of oxygen and sulfur; M is selected from the group consisting of lithium and potassium; and n is an integer from 1 to 3.

7 Claims, No Drawings

PROTECTED DERIVATIVES OF THE ENONE OF SPECTINOMYCIN

CROSS REFERENCE TO RELATED APPLICATIONS

The present application is a continuation-in-part of International Patent Application PCT/US90/04451, filed Aug. 14, 1990, now abandoned, which is a continuation of U.S. Ser. No. 07/406,912, filed Sep. 13, 1989, now abandoned.

FIELD OF THE INVENTION

This invention concerns a process for alkylating in the gamma position a protected derivative of the enone of spectinomycin to form intermediate compounds useful in the synthesis of 6'-alkyl-spectino-mycins. 6'-Alkylspectinomycins and methods for preparing them are disclosed in U.S. Pat. Nos. 4,351,771, 4,420,624 and 4,532,336. The 6'-alkylspectinomycins are known to exhibit especially good antibacterial activity.

INFORMATION DISCLOSURE

It is well documented in the literature that alpha-beta unsaturated ketones are selectively alkylated in the alpha position over the gamma position (see, for example, Zimmerman in "Molecular Rearrangements" ed. de Mayo, Interscience, New York, p. 345 (1963). Rathke and Sullivan in Tet. Let., 41, pp. 4249, 4257 (1972) teaches that the corresponding lithium enolates of alpha-beta unsaturated esters will be selectively alkylated in the alpha position by alkyl halides. de Graf et al in Tet. Let., 17, p. 1653, 1655 (1974) teaches that various alkylating agents, including allyl halides, will selectively alkylate the corresponding lithium enolates of alpha-beta unsaturated aldehydes in the alpha position.

Katzenellenbogen and Crumine in J. Am. Chem. Soc. (JACS), 96, pp. 5662-5663 (1974) and in JACS, 98, pp. 4925-4928 (1976) teaches that the addition of cuprous iodide to form the copper dienolate of alpha-beta unsaturated esters results in an enhanced selectivity for gamma alkylation (where the alkylating agent is an allylic halide), compared to lithium dienolates which undergo exclusive alpha alkylation. The same kind of gamma alkylation selectivity for copper dienolates derived from alpha-beta unsaturated acids is taught by Savu and Katzenellenbogen in J. Org. Chem., 46, pp. 239-240 (1981). Majewski, et. al. in J. Org. Chem., 46, p. 2029 (1981) also teaches enhanced gamma alkylation specificity for some alpha-beta unsaturated amides.

Gamma alkylations on lithium enaminoketone enolates in which the nitrogen is beta to the carbonyl ketone have been disclosed in Yoshimoto, et. al., Tet. Let., 1, pp. 39-42 (1973). In this reference the alkylating agents were not allyl halides. Bryson and Gammill in Tet. Let., 45, pp. 3963-3966 discloses exclusive gamma alkylation of lithium enamineketone enolates in which a variety of alkylating agents were used. This reference also teaches that lithium diisopropylamide is a better Anion generating species than n-butyllithium for gamma-alkylation of enaminoketones. However, Gammill and Bryson in Synthesis, pp. 401-403 (1978) teaches that when nitrogen is replaced by oxygen, alpha alkylation predominates.

Smith and Scarborough in Tet. Let., 44, p. 4193 (1975) report that alkylation of lithium enolates (using LDA) derived from 3(2H)-furanones occurs exclusively in the alpha' position. Furthermore, complete substitution in the alpha' position results in exclusive gamma alkylation. These enones contain beta oxygens similar to the spectinomycin system; however, the enone closest to spectinomycin gives only a 2:1 selectivity for gamma alkylation over alpha alkylation (spectinomycin results in only gamma alkylation). This reference reports that gamma alkylation occurred in all cases where the corresponding dienolate contained a double bond exocyclic to the ring (no gamma alkylation occurred in enolates containing endocyclic or acyclic double bonds).

Stork and Danheiser in J. Org. Chem., 38, p. 1775 (1973) also teach gamma alkylation of enamines; however, polyalkylation was not reported to be a problem.

SUMMARY OF THE INVENTION

The present invention provides:

A process for preparing a compound having the formula III which comprises reacting a compound having the formula V with a strong base and an alkenyl halide, wherein $R_1$ is selected from the group consisting of alkoxycarbonyl, halogenated alkoxycarbonyl, aralkoxycarbonyl, and arylsulfone; $R_2$ is selected from the group consisting of hydrogen, trimethylsilyl (TMS), tetrahydropyran (THP), and triethylsilyl (TES); A is selected from the group consisting of oxygen and sulfur; M is selected from the group consisting of lithium and potassium; and n is an integer from 1 to 3.

Another aspect of the invention is the compound of Formula III and the enolate IV.

A protected derivative of the enone of spectinomycin is selectively alkylated in the gamma position to form 6'-alkylated derivatives useful in the synthesis of spectinomycin analogs, in particular the antibiotic trospectomycin. This particular process is advantageous since the 6'-alkylated intermediate is difficult to obtain by other methods. Furthermore, this new process results in an improved overall yield in the synthesis of trospectomycin when compared to a prior process for synthesizing trospectomycin.

DETAILED DESCRIPTION OF INVENTION

The process of this invention utilizes a strong base as the anion generating species and alkenyl halides or methyl iodide as the electrophilic alkylating species. Alkylation in the gamma position is exclusive over the alpha position—a significant advantage over the prior art where gamma selectively for compounds closest to the spectinomycin compound resulted in a 2:1 selectively. Furthermore, gamma alkylation of the spectinomycin enone does not require the presence of copper salts. This, too, is an advantage over the prior art, where the addition of copper salts has been found to cause or enhance gamma selectivity. Polyalkylation at the gamma position is a problem; however, the addition of copper (or lithium) salts may be useful in decreasing the amount of polyalkylation that does occur.

The numbering of carbons shown in compound I will be used in discussions thereof throughout the specification.

"$C_1$-$C_4$ alkyl" means methyl, ethyl, propyl and isopropyl.

"$C_3$-$C_4$ alkenyl" means propenyl, butenyl, pentenyl and isomeric forms thereof.

"Aryl" means p-methylphenyl, p-methoxyphenyl, halophenyl, naphthyl, and anthracene.

"Halogenated alkoxycarbonyl" means mono-, di-, tri-halomethoxycarbonyl; mono-, di, tri-haloethoxycarbonyl; mono-, tri-halopropoxycarbonyl; mono-, di-, tri-halobutoxycarbonyl; mono-, di-, tri-halopentoxycarbonyl; and isomeric forms thereof.

"Halo" means bromo, chloro, iodo and fluoro.

"Halide" means iodide and bromide.

"Aralkoxycarbonyl" means benzyloxycarbonyl (Cbz), phenylthoxycarbonyl, phenylpropoxycarbonyl, diphenyloctoxycarbonyl, and isomeric forms thereof and fluoroenylmethoxy carbonyl.

"Alkoxycarbonyl" means isopropyloxy carbonyl, tertiary-butyloxy carbonyl, and tertiary-pentyloxycarbonyl.

"Alkenyl halide" means allyl halide, n-propenyl halide, n-butenyl halide and branched and substituted alkenyl halides.

The process comprises reacting spectinomycin enone V with a strong base and an alkenyl halide. While the operability of the process is not dependent upon the order of mixing the alkenyl halide and the strong base with the enone V, a preferred method of conducting the process is illustrated schematically below.

In Step 1 the protected spectinomycin enone V (1.0M) is dissolved in solvent, and the solution is degassed by evacuating and flushing with nitrogen gas. The solution is then cooled, and lithium hexamethyldisilamide (LiHMDS) and potassium hexamethyldisilamide (KHMDS) (0.10 eq. to 3 eq. in solvent) is added to yield the enolate IV. Any strong base will work; however, lithium amides with high oxidation potentials such as LiHMDS are preferred. The temperature range for this reaction is between $-70°$ and $+65°$ C., with the best results occurring at about $-40°$ C. The ratio of strong base to enone is about 1:3 with the preferred ratio being about 1.75:1. Solvents that can be used include THF, toluene, DME, diethyl ether, MeOtBu, dioxane, heptane and mixtures thereof. Any solvent relatively inert to strong base would be expected to work. The enolate IV can be recovered by crystallization, extraction, chromatography or combinations thereof or may be reacted in Step 3 without isolation.

The starting enone V used in the process may be prepared by procedures known in the art, i.e., D. White et al in *Tet. Let.*, pp. 2737–2740 (1979).

In Step 2, enolate IV is reacted with alkenyl halide to yield 6'-alkenylspectinomycin enone III. The ratio of reactants is about 1:5 equivalents of alkenyl halide to one equivalent of enolate.

Compound III can be recovered by crystallization, extraction, chromatography, or combinations thereof or may be reacted in Step 3 without isolation.

In Step 3 6'-alkenylspectinomycin enone III is subjected to reduction to yield protected 6'-alkylspectinomycin II.

In Step 4, the compound of Formula II is deprotected to yield 6'-alkylspectinomycin I. Steps 3 and 4 are conducted according to the procedures for reduction and deprotection well known in the art, for example, U.S. Pat. No. 4,532,336 (Scheme 1), and that scheme is herein incorporated by reference. When the protecting group on $R_1$ of the enone is arylsulfoxide ($ArSO_2$), deprotection can be accomplished by photochemistry according to methods well known in the art, for example, Osamu Vonemitsu et al, JACS (1950), 102, p. 3978.

The following preparations of intermediates in the process as well as the intermediates themselves are indicative of the scope of the invention and are not to be construed as limitive. Those skilled in the art will promptly recognize variations from the reaction conditions and techniques of the invention process.

EXAMPLE 1

Tri-methyl-silyl-bis-benzyloxycarbony-6'-alkyl-spectinomycin

The tri-methylsilyl-bis-benzyloxycarbonyl enone (30 gm) is dissolved in THF (60 ml), and the solution is degassed by evacuating and flushing with nitrogen gas. The solution is then cooled to $-20°$ C. and LiHMDS (1.0M in THF, 44 ml) is added over a period of five minutes. The resulting red-brown solution is then warmed to 10° C., and allyl iodide (4.45 gm) is added all in one portion. The mixture is stirred at 10°–20° C. for one hour, after which methanol (30 ml) and 50% aqueous HCl (30 ml) is added to the mixture. The solution is then stirred at room temperature for one hour. Ethyl acetate (60 ml) and water (30 ml) are then added. The phases are separated, and the organic layer washed with saturated salt water and concentrated to dryness under vacuum. This procedure provides 23.1 gm of the impure title compound (VI). The title compound may then be purified by column chromatography.

$^{13}C$ Data for the title compound:
187(s), 178(s), 156(s), 136(s), 135(d), 129(d), 128(d), 127(d), 116(t), 100(d), 98(d), 86(s), 74(d), 73(d), 67.5(d), 67(t), 659(d), 63(d), 56(d), 34(t) 31(q), 30(d).

$^{13}C$ Data for the intermediate dienolate: 155(s), (146)s, 139(s), 136(s), 128(s), 127(s), 126(s), 117(t), 111(d), 46(d), 89(s), 73(d), 72(d), 70(d), 67(d), 66(t), 58(d) 31(q), 30(q), 1.8(q), 1.0(q), 0.7(q), ppm.

EXAMPLE 2

Tri-tetrahydropyran-bis-benzyloxycarbonyl-6'-alkyl-spectinomycin 0.411 ml of 1.0 LiHMDS in THF is added to a solution of 0.10 gm of enone (R1=Cbz, R2=THP) dissolved in 5 ml of THF. The mixture is stirred at 23° C. for 45 minutes. 71 mg of allyl bromide is added all in one portion, and the mixture is heated to 40° C. for two hours. The solvent is removed under reduced pressure to provide a red foam. The residue is dissolved in methylene chloride, and the organic solution is washed with a saturated aqueous bicarbonate solution, dried over sodium sulfate, and concentrated to a yellow solid. The crude product is purified by chromatography over silica gel, resulting in 62 mg of the title compound as a clear oil.

EXAMPLE 3

Trimethylsilyl-bis-benzyloxycarbonyl-6'-alkylspectinomycin 1.0M LiHMDS in THF is added to a solution of 0.2 gm of trimethylsilyl-bis-benzyloxycarbonylenone (R1=Cbz, R2=TMS) dissolved in 0.5 ml of 1,2-dimethoxyethane. The resulting red solution is stirred at 23° C. for 45 minutes. 0.103 gm of allyl iodide is added, and the mixture is stirred at 23° C. for 16 hours. The reaction is worked up as described in Example 1 to provide a 53% yield of title compound.

EXAMPLE 4

Trimethylsilyl-bis-benzyloxycarbonyl-6'-alkylspectinomycin

A solution of 10.0 gm of trimethylsilyl-bis-benzyloxycarbonylenone (R1=Cbz,R2=TMS) dissolved in 20 ml of THF is cooled to −70° C. 17.2 ml of a 1.0M solution of LiHMDS in THF is added in one portion to this solution. CuCN (1.09 gm) is added, and the mixture is stirred at −70° C. for 60 minutes. The cooling bath is then removed. When the temperature reaches 15° C., 1.35 ml of allyl iodide is added all in one portion. After 10 minutes at 15° C., the reaction is quenched by the addition of 10 ml of methanol and 10 ml of 6N HCl. After one hour of stirring, the mixture is diluted with 50 ml of ethyl acetate and 50 ml of water. The organic phases are separated and washed with saturated sodium chloride, dried over sodium sulfate, and concentrated to dryness. The crude title compound yield is 95.2% and may be purified by chromatography.

EXAMPLE 5

Trimethylsilyl-bis-benzyloxycarbonyl-6′-alkylspectinomycin

A solution of 75 mg of trimethylsilyl-bis-benzyloxycarbonylenone (R1=Cbz, R2=TMS) dissolved in 3.0 ml of THF is warmed to 40° C., to which methyl iodide is then added. 0.5 ml of a 1.0M solution of LiHMDS in THF is added all in one portion. After one hour at 40° C. the reaction is worked up as described in Example 1 to yield the title compound.

EXAMPLE 6

Trimethylsilyl-bis-tosyl-6′-alkylspectinomycin

A solution of 10 gm of trimethylsilyl-bis-tosyle none (R1=p-toluenesulfone (tos), R2 =TMS) in 20 ml of THF is cooled to −30° C. 12 ml of a 1.0M solution of LiHMDS in THF is added all in one portion, and the mixture is warmed to 5° C. 2.02 gm of allyl iodide is added all in one portion. After 30 minutes, 10 ml of methanol is added, followed by 10 ml of 6N HCl. The mixture is stirred at room temperature for one hour. 25 ml of ethyl acetate is added, followed by 25 ml of water. The organic phase is separated and washed with 1N HCl, water, and saturated sodium chloride. The organic phase is then concentrated to about 20 ml. 20 ml of toluene is added and the mixture is concentrated to about 25 ml. The crystalline product is collected by filtration and dried in a vacuum oven at 60° C. overnight to provide 3.64 gm of the title compound.

EXAMPLE 7

Trimethylsilyl-bis-benzyloxycarbonyl-6′-alkylspectinomycin

A solution of 83 mg of diisopropylamine in 3 ml of THF is cooled to 0° C. 0.172 ml of a 2.5M solution of nBuLi in hexane is added all in one portion to the solution. 0.1 gm of Trimethylsilyl-bis-benzyl-oxycarbonyl enone (R1=Cbz, R2=TMS) dissolved in 3 ml of THF is added to the mixture. 74 mg of allyl bromide is then added and the mixture is warmed to 45° C. After 30 minutes at 45° C., the reaction is worked up as described in Example 1 to provide the title compound.

EXAMPLE 8

Conversion to trospectomycin

The product from Example 1 is dissolved in methanol (230 ml) and water (25 ml) is added. 3% Pd on BaCO3 (4.5 g) is added and the mixture cooled to −20° C. and stirred under hydrogen (90 p.s.i.) for 30 hours. The resulting slurry is filtered through powdered cellulose while kept at −20° C. Sulfuric acid (2N) is added until the pH is in the range of 2.5–3.5. The mixture is then stirred for three hours at −20° C. and the product collected by filtration.

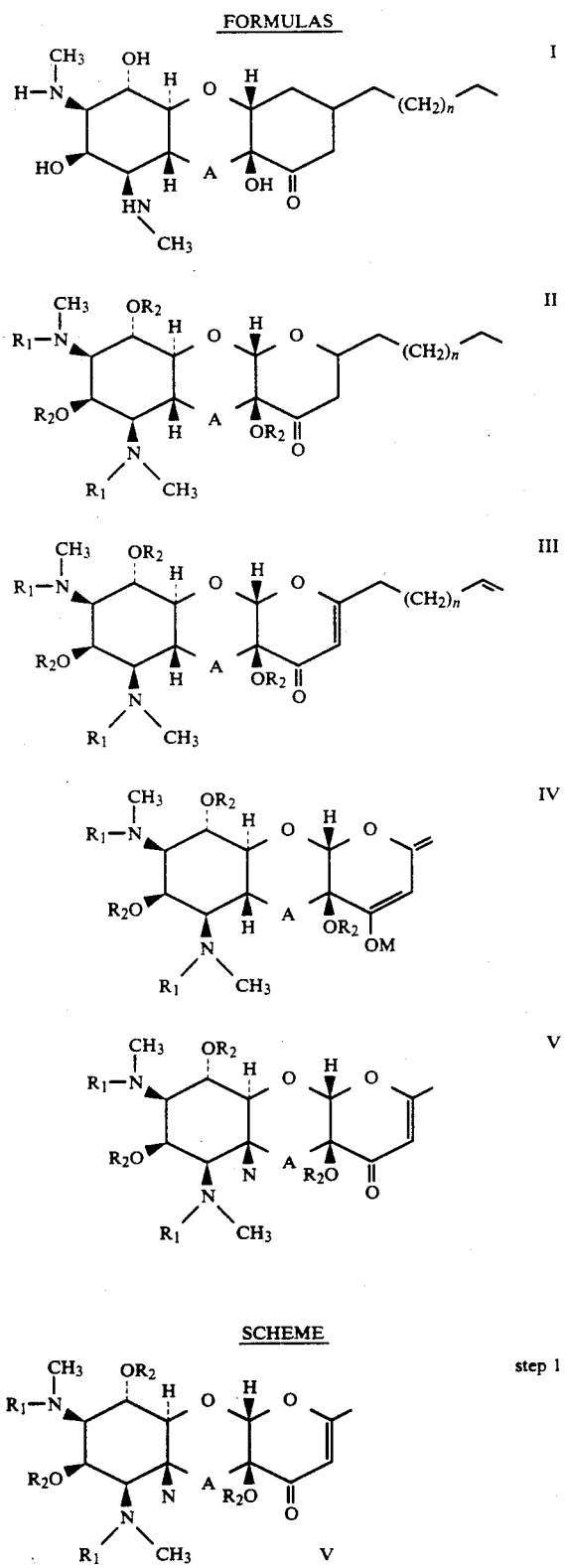

-continued

SCHEME

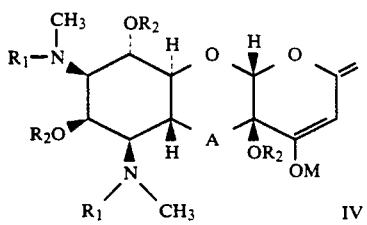
IV

↓

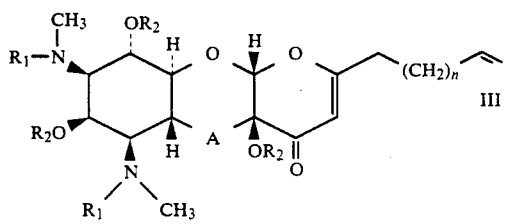
III

↓ step 4

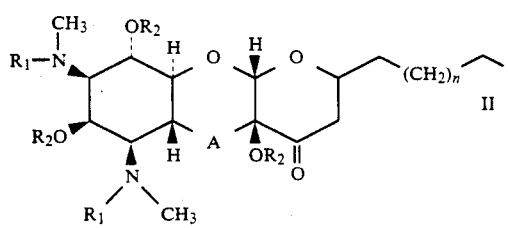
II

↓

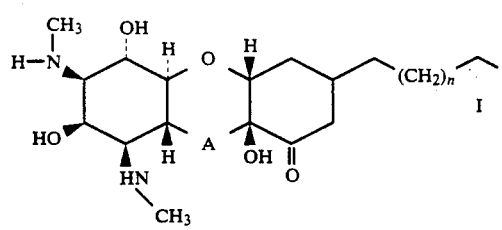
I

I claim:

1. A compound having the formula

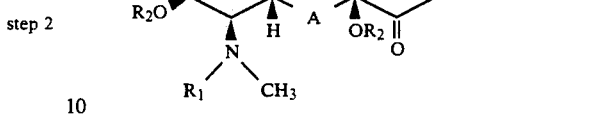
III step 2

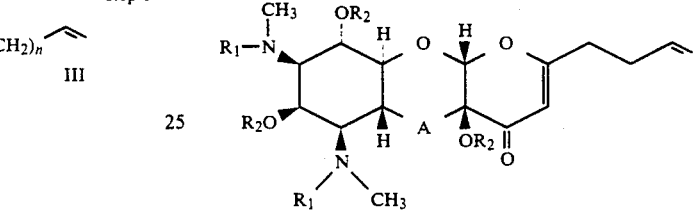
10 wherein $R_1$ is selected from the group consisting of benzyloxycarbonyl and 4-methylphenylsulfone; $R_2$ is selected from the group consisting of trimethylsilyl, triethylsilyl, and tetrahydropyran; A is selected from the group consisting of oxygen and sulfur; and n is an integer from 1 to 3.

2. A compound according to claim 1 having the formula step 3

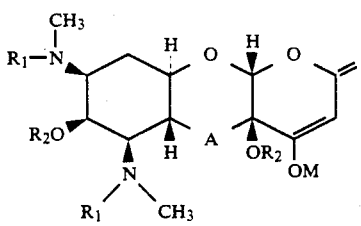
VI wherein $R_1$ and $R_2$ are the same as in claim 11.

3. A compound according to claim 1 where $R_1$ is benzyloxycarbonyl and $R_2$ is trimethylsilyl.

4. A compound according to claim 1 where $R_1$ is benzyloxycarbonyl and $R_2$ is tetrahydropyran.

5. A compound having the formula wherein $R_1$ is selected from the group consisting of alkoxycarbonyl, halogenated alkoxycarbonyl, aralkoxycarbonyl, and arylsulfone; $R_2$ is selected from the group consisting of hydrogen, trimethylsilyl (TMS), tetrahydropyran (THP), and triethylsilyl (TES); A is selected from the group consisting of oxygen and sulfur; M is selected from the group consisting of lithium and potassium; and n is an integer from 1 to 3.

6. A compound according to claim 5 wherein $R_1$ is benzyloxycarbonyl, $R_2$ is tetrahydropyran and M is lithium.

7. A compound according to claim 5 wherein $R_1$ is benzyloxycarbonyl, $R_2$ is trimethylsilyl and M is lithium.

* * * * *